United States Patent
Henriet et al.

(10) Patent No.: US 6,538,156 B1
(45) Date of Patent: Mar. 25, 2003

(54) METHOD FOR PURIFYING ADIPIC ACID BY CRYSTALLIZATION

(75) Inventors: Eric B. Henriet, Lyons (FR); Philippe Leconte, Meyzieu (FR); Carl Patois, Lyons (FR); Robert Perron, Charly (FR)

(73) Assignee: Rhodia Fiber & Resin Intermediates, Courbevoie Cedex (FR)

( * ) Notice: Subject to any disclaimer, the term of this patent is extended or adjusted under 35 U.S.C. 154(b) by 0 days.

(21) Appl. No.: 09/194,925

(22) PCT Filed: May 29, 1997

(86) PCT No.: PCT/FR97/00939

§ 371 (c)(1),
(2), (4) Date: Dec. 4, 1998

(87) PCT Pub. No.: WO97/46510

PCT Pub. Date: Dec. 11, 1997

(30) Foreign Application Priority Data

Jun. 4, 1996 (FR) .............................. 96 07171

(51) Int. Cl.$^7$ .......................... C07C 51/43; C07C 55/14
(52) U.S. Cl. ...................................... 562/593; 562/590
(58) Field of Search .................................. 562/590, 593

(56) References Cited

U.S. PATENT DOCUMENTS

| | | | |
|---|---|---|---|
| 2,862,027 A | 11/1958 | Feldman | 260/533 |
| 3,207,783 A | * 9/1965 | Carter | 260/537 |
| 5,166,421 A | * 11/1992 | Bruner, Jr. | 562/522 |
| 5,292,944 A | * 3/1994 | Atadan et al. | 562/590 |

FOREIGN PATENT DOCUMENTS

| | | |
|---|---|---|
| FR | 901 841 | 8/1945 |
| FR | 1 349 134 | 12/1963 |

\* cited by examiner

*Primary Examiner*—James O. Wilson
*Assistant Examiner*—Leigh C. Maier
(74) *Attorney, Agent, or Firm*—Burns, Doane, Swecker & Mathis, L.L.P.

(57) ABSTRACT

The invention discloses a method for purifying adipic acid by crystallization or recrystallization in at least one carbolyxic acid. More precisely, it discloses an improvement in adipic acid crystallization or recrystallization, characterised in that the said crystallization or recrystallization is effected in at least one carboxylic acid with a melting point below 20° C. The presence of carbon monoxide during crystallization or recrystallization can have a favourable effect on the adipic acid purity, in particular by reducing the content of metal catalyst traces of the adipic acid. The adipic acid purity can also be improved when the crystallization or recrystallization is effected in presence of a strong proton acid.

12 Claims, No Drawings

METHOD FOR PURIFYING ADIPIC ACID BY CRYSTALLIZATION

The present invention relates to a process for purifying adipic acid by crystallization or recrystallization from at least one carboxylic acid.

Adipic acid is one of the two base materials for preparing polyamide 6-6. For the applications of polyamide 6-6 it is necessary to have a very high purity, and this purity must exist already at the stage of the precursors, especially at the adipic acid stage.

Depending on the process by which adipic acid is prepared the impurities it contains are obviously different. The present process can be applied to adipic acid originating from various processes of synthesis. In fact, one of the most troublesome and sometimes most costly impurities is formed by the presence of traces of the catalyst employed during the preparation of adipic acid.

However, in the description which follows, the process will be applied more particularly to adipic acid obtained from the double hydroxycarbonylation of butadiene or from the oxidation of cyclohexane.

The first hydroxycarbonylation of butadiene leads to a mixture of pentenoic acids, principally 3-pentenoic acid. The second hydroxycarbonylation affects the pentenoic acids obtained in the first reaction and leads to adipic acid which also includes a certain amount of 2-methylglutaric acid, 2-ethylsuccinic acid and other compounds originating from the first hydroxycarbonylation reaction, such as gamma-valerolactone, unconverted pentenoic acids, and methylbutenoic acid. It also includes traces of the catalyst employed in the second hydroxycarbonylation reaction, usually iridium and/or rhodium.

The direct oxidation of cyclohexane to adipic acid is generally carried out in the presence of cobalt, and in this process the adipic acid obtained contains traces of cobalt catalyst.

Since adipic acid is of low solubility in water when cold but is much more soluble when hot, this solvent is generally employed for the crystallization of the said acid.

However, owing to the very high purities which are increasingly required for adipic acid, especially insofar as trace metals are concerned, one or even a number of recrystallizations from water often prove to be inadequate.

Besides the trouble which can be caused by the presence of trace metals to the various uses of adipic acid, the intrinsic value of certain catalysts, such as iridium or rhodium, bearing in mind the very large tonnages of adipic acid, means that it is essential to recover them as thoroughly as possible in the context of an economically viable industrial process.

The present invention consists in an improved process for crystallization or recrystallization of adipic acid, characterized in that the said crystallization or recrystallization is carried out in at least one carboxylic acid having a melting point of less than 20° C.

The carboxylic acids employed in the present process are, more particularly, aliphatic carboxylic acids which are saturated or which contain an ethylenic unsaturation.

They are preferably linear or branched monocarboxylic acids having 2 to 6 carbon atoms.

As nonlimitative examples of such monocarboxylic acids mention may be made of acetic acid, propionic acid, butanoic acids, pentanoic acids, hexanoic acids and pentenoic acids.

Acetic acid and pentenoic acids are preferred, acetic acid owing to its availability and to its use in the synthesis of adipic acid from cyclohexane, and pentenoic acids because they are an intermediate in the preparation of adipic acid from butadiene.

The purity of the adipic acid recrystallized in this way may be improved further when recrystallization is carried out in the presence of carbon monoxide.

The carbon monoxide can make up at least part of the atmosphere above the solution in the crystallization or recrystallization reactor (or reactor headspace) or can create within the said reactor a pressure which is greater than the atmospheric pressure.

In practice, the process will therefore be operated under an absolute pressure of from 0 bar (preferably at least 0.5 bar) to 50 bars of carbon monoxide, the upper limit not being critical in nature but being representative of industrial apparatus which is not excessively expensive.

The crude adipic acid subjected to recrystallization according to the present process is usually an adipic acid which has already undergone one or more purification treatments, in particular by crystallization from water, by refining or else by distillation, to give it a minimum purity of approximately 95%.

Generally, the adipic acid recrystallized by the process of the invention has a purity of from 95 to 99.95%.

The recrystallization consists in taking the adipic acid to be purified and dissolving it in the minimum amount of hot aliphatic carboxylic acid, i.e. usually at a temperature from 80 to 250° C., optionally under an at least partial pressure or atmosphere of carbon monoxide, and in then inducing crystallization of the dissolved adipic acid by cooling the solution, optionally after having seeded the solution using crystals of pure adipic acid.

Generally, the quantity of carboxylic acid employed is that which leads to a saturated solution of adipic acid at the chosen temperature. By way of indication, at 90° C. the saturated solution in 3-pentenoic acid contains approximately 33% of adipic acid by weight per weight.

The catalyst content of the adipic acid can also be reduced when recrystallization is carried out in the presence of a strong protic acid.

By strong protic acid is meant in the present text an inorganic protic acid having a pKa of less than 1.

As nonlimitative examples of such strong protic acids mention may be made of hydroiodic acid, hydrobromic acid, hydrochloric acid, nitric acid and sulphuric acid.

The quantity of strong protic acid can vary from 0 mol to 100 mol per mole of catalyst metal present in the adipic acid. Preferably, the quantity of protic acid varies from 0 mol (more preferably from 1 mol) to 50 mol per mole of catalyst metal.

The process of the invention likewise embraces the crystallization of adipic acid from reaction mixtures in which it is present.

It is thus possible, for example, to crystallize adipic acid from the mixture obtained by hydroxycarbonylation of pentenoic acid with water and carbon monoxide. This reaction mixture can be mixed with the carboxylic acid in the presence or absence of the carbon monoxide employed for the hydroxycarbonylation reaction, and the whole mixture can be kept at a temperature from 80 to 250° C. as indicated above for the recrystallization.

Crystallization can also be carried out in the hydroxycarbonylation reactor by allowing the reaction mixture to cool, preferably under carbon monoxide pressure. This variant can be employed in particular when hydroxycarbonylation is conducted in a carboxylic acid or when it is conducted in 3-pentenoic acid with a degree of conversion of the latter which is incomplete.

Since the hydroxycarbonylation reaction is conducted in the presence of carbon monoxide, it is not generally necessary to add this compound for the crystallization, although this possibility is not excluded if appropriate.

Similarly, since the promoter used in the hydroxycarbonylation reaction may be hydroiodic acid or hydrobromic acid, it may not be necessary to add the strong protic acid. However, if desired, the quantity of strong protic acid present in the reaction mixture may be supplemented. As for the recrystallization of adipic acid, it is also possible to operate in the absence of strong protic acid, although this variant is not preferred.

The recrystallization according to the invention can be carried out a number of times in succession on the adipic acid in order to reduce further the content of catalyst metal. It is also possible to follow a crystallization or recrystallization according to the invention by one or more recrystallizations from water.

The examples which follow illustrate the invention.

EXAMPLE 1

A glass bulb is charged with 5.2 g of adipic acid, containing 31.2 µg of Co (0.0006% by weight per weight of adipic acid), and 7.5 ml of acetic acid. The adipic acid has been prepared by direct oxidation of cyclohexane in the presence of Co acetate and has been purified by recrystallization from water. It does not contain any measurable quantities of organic impurities.

The open bulb is placed in a 125 ml autoclave, which is then closed.

The headspace is filled cold with nitrogen (approximately 1 bar).

The temperature is raised to 185° C. and is maintained at this level for approximately 30 minutes.

After cooling the autoclave and purging it with nitrogen, the adipic acid is filtered off and the autoclave is rinsed with a few ml of acetic acid.

The adipic acid filtered off is washed with 2 times 5 ml of acetic acid and then 3 times 8 ml of acetic acid.

The adipic acid is dried overnight in an oven (60° C.). The cobalt present in the final adipic acid is assayed by inductively coupled plasma in conjunction with mass spectrometry (ICP/mass). 0.00008% of Co by weight per weight is found.

EXAMPLE 2

Example 1 is repeated with the same charges and under the same operating conditions but with the addition to the reaction mixture employed of 10 molar equivalents of HCl per molar equivalent of Co present in the adipic acid employed.

The same treatment as for Example 1 gives a dry final adipic acid containing 0.000009% of Co by weight per weight.

EXAMPLES 3 TO 8

Example 1 is repeated under the same operating conditions but with the addition to the reaction mixture employed of HI (with a molar ratio of HI to Ir as indicated in Table 1 below), with the use of 3-pentenoic acid (P3) as the recrystallization solvent, and with the use of an adipic acid (AdOH) containing iridium. The adipic acid was prepared by hydroxycarbonylation of 3-pentenoic acid in the presence of a catalyst based on Ir and was purified by recrystallization from water. It contains no measurable quantities of organic impurities.

Following recrystallization, the adipic acid is washed with 3-pentenoic acid saturated with adipic acid and then with water saturated with adipic acid.

Table 1 below summarizes the conditions under which the examples were carried out (Tp=temperature) and the initial and final contents of Ir (initial Ir and final Ir), expressed in micrograms per gram, of the adipic acid employed.

TABLE 1

| Example | AdOH in g | P3 in g | Tp in ° C. | Duration in min | CO in bars | Molar ratio HI:Ir | Initial Ir | Final Ir |
|---|---|---|---|---|---|---|---|---|
| Ex. 3 | 2.7 | 3.9 | 185 | 20 | 30 | 10 | 5.0 | 0.76 |
| Ex. 4 | 1.43 | 2.0 | 90 | 120 | 30 | 10 | 5.0 | 2.6 |
| Ex. 5 | 5.2 | 7.8 | 185 | 30 | 30 | 20 | 2.2 | 0.42 |
| Ex. 6 | 6.2 | 9.3 | 185 | 30 | 1 | 20 | 2.2 | 0.56 |
| Ex. 7 | 2.9 | 4.5 | 185 | 1200 | 1 | 10 | 0.46 | 0.18 |
| Ex. 8 | 8.05 | 13 | 185 | 40 | 1 | 20 | 8.0 | 1.3 |

EXAMPLES 9 TO 12

Examples 3 to 8 are repeated but using an adipic acid (AdOH) containing rhodium. The adipic acid was prepared by hydroxycarbonylation of 3-pentenoic acid in the presence of a catalyst based on Rh and was purified by recrystallization from water. It contains no measurable quantities of organic impurities.

Following recrystallization, the adipic acid is washed with 3-pentenoic acid saturated in adipic acid and then with water saturated in adipic acid.

Table 2 below summarizes the conditions under which the examples were carried out (Tp=temperature) and the initial and final contents of Rh (initial Rh and final Rh), expressed in micrograms per gram, of the adipic acid employed.

TABLE 2

| Example | AdOH in g | P3 in g | Tp in °C. | Duration in min | CO in bars | Molar ratio HI:Rh | Initial Rh | Final Rh |
|---|---|---|---|---|---|---|---|---|
| Ex. 9 | 4.99 | 7.5 | 190 | 30 | 30 | 10 | 9.5 | 3.2 |
| Ex. 10 | 5.02 | 7.5 | 190 | 30 | 1 | 13 | 9.5 | 3.1 |
| Ex. 11 | 5.04 | 7.5 | 190 | 30 | 0 (1 bar of argon) | 12 | 9.5 | 3.8 |
| Ex. 12 | 5.05 | 7.5 | 190 | 600 | 1 | 14 | 9.5 | 0.46 |

EXAMPLE 13

In Example 13, the recrystallization described for Examples 3 to 8 is repeated using the recrystallized adipic acid obtained in Example 7.

Table 3 below summarizes the conditions under which the example was carried out and the initial and final contents of Ir (initial Ir and final Ir), expressed in micrograms per gram, of the adipic acid employed.

COMPARATIVE TEST 1

An adipic acid obtained by hydroxycarbonylation of 3-pentenoic acid in the presence of iridium and HI is recrystallized from water. This adipic acid has already undergone one crystallization and still contains 0.00022% of iridium.

The recrystallization is carried out conventionally by dissolving adipic acid in the minimum amount of water at approximately 95° C. and then by gradual cooling of the resulting solution, followed by filtration and, finally, by washing of the adipic acid filtered off with 2 times 5 ml of water and with 3 times 8 ml of water.

The adipic acid is dried overnight in an oven (60° C.). The iridium present in the final adipic acid is assayed. 0.00022% of Ir by weight per weight is found. Therefore, the iridium content of the adipic acid has not been successfully reduced.

TABLE 3

| Example | AdOH in g | P3 in g | Tp in °C. | Duration in min | CO in bars | Molar ratio HI:Rh | Initial Rh | Final Rh |
|---|---|---|---|---|---|---|---|---|
| Ex. 13 | 1.26 | 2.0 | 185 | 30 | 1 | 30 | 0.18 | 0.14 |

EXAMPLE 14

The hydroxycarbonylation of 3-pentenoic acid is carried out with the following charges:
77.7 g of 3-pentenoic acid
88.1 mg of $[IrCl(COD)]_2$
169.6 mg of a 57% by weight aqueous solution of HI
5.7 g of water, injected continuously.

The carbon monoxide pressure at the reaction temperature (185° C.) is maintained at 22 bars and the reaction is stopped after a period of 1 h 5 minutes.

After gradual cooling under the carbon monoxide pressure of 22 bars, the crystallized adipic acid is drawn off and filtered. Assay by gas chromatography and by high-performance liquid chromatography of the compounds of the filtrate is then used to determine a degree of conversion of the 3-pentenoic acid of 56.6%.

The adipic acid crystallized in this way contains 0.000122% of iridium.

This adipic acid is recrystallized from 3-pentenoic acid under a carbon monoxide atmosphere (circulation bubble by bubble).

After recrystallization, the adipic acid is washed with 3-pentenoic acid saturated with adipic acid and then with water saturated with adipic acid.

The recrystallized and dried adipic acid has an iridium content of 0.00002% by weight per weight.

What is claimed is:

1. A process for purifying adipic acid to reduce the content of trace metals therein, said adipic acid having a purity of at least 95% and being obtained by hydroxycarbonylation of pentenoic acids with water and carbon monoxide, said process comprising the steps of:
   (a) dissolving the adipic acid in at least one hot carboxylic acid having a melting point of less than 20° C. to form a solution; and
   (b) cooling the solution to induce crystallization of the dissolved adipic acid.

2. The process according to claim 1, wherein step (a) is carried out at a temperature from 80 to 250° C.

3. The process according to claim 1, wherein the carboxylic acid comprises aliphatic carboxylic acids which are saturated or which contain an ethylenic unsaturation.

4. The process according to claim 3, wherein the carboxylic acid comprises linear or branched monocarboxylic acids having 2 to 6 carbon atoms.

5. The process according to claim 1, wherein the carboxylic acid is selected from acetic acid, propionic acid, butanoic acids, pentanoic acids, hexanoic acids, and pentenoic acids.

6. The process according to claim 1, wherein step (a) is carried out in the presence of carbon monoxide.

7. The process according to claim 6, wherein step (a) is carried out under an absolute pressure of from 0.5 bar to 50 bars of carbon monoxide.

8. The process according to claim 1, wherein the adipic acid in step (a) has a purity of 95 to 99.95%.

9. The process according to claim 1, wherein step (a) is carried out in the presence of a strong protic acid.

10. The process according to claim 9, wherein the strong protic acid is selected from hydroiodic acid, hydrobromic acid, hydrochloric acid, nitric acid, and sulfuric acid.

11. The process according to claim 9, wherein the strong protic acid is present in an amount up to 100 mol per mole of trace metals present in the adipic acid.

12. The process according to claim 11, wherein the strong protic acid is an amount up to 50 mol per mole of trace metals present in the adipic acid.

* * * * *